United States Patent [19]
Williams et al.

[11] Patent Number: 5,496,092
[45] Date of Patent: Mar. 5, 1996

[54] MULTI-POSITION PEDIATRIC IMMOBILIZER AND TRANSPORT DEVICE

[75] Inventors: Gary R. Williams, Carlsbad, Calif.; Irvin D. Pollock, Wilmington, Ohio

[73] Assignee: Gary R. Williams, Carlsbad, Calif.

[21] Appl. No.: 231,851

[22] Filed: Apr. 25, 1994

Related U.S. Application Data

[63] Continuation of Ser. No. 879,852, May 6, 1992, abandoned.
[51] Int. Cl.⁶ .............................. A47D 1/10; B60N 2/28
[52] U.S. Cl. .................. 297/250.1; 297/256.13; 297/354.13; 297/365; 297/464
[58] Field of Search ........................ 297/250.1, 256.13, 297/352, 365, 380, 382, 464, 484, 485, 30, 363, 364, 354.13

[56] References Cited

U.S. PATENT DOCUMENTS

| | | |
|---|---|---|
| 221,124 | 10/1879 | Stevens .................... 297/30 X |
| 262,311 | 8/1882 | Ortlepp .................... 297/365 |
| D. 285,383 | 9/1986 | Anthony . |
| 1,224,982 | 5/1917 | Washeim .................. 297/365 |
| 1,271,515 | 7/1918 | Murray ................... 297/464 X |
| 1,415,626 | 5/1922 | Fuchs . |
| 2,769,483 | 11/1956 | Peterson ................. 297/464 X |
| 3,921,231 | 11/1975 | Bourgraf et al. . |
| 4,058,342 | 11/1977 | Ettridge . |
| 4,181,356 | 1/1980 | Fleischer . |
| 4,265,481 | 5/1981 | Fleisher ..................... 297/30 |
| 4,274,674 | 6/1981 | Deloustal . |
| 4,521,052 | 6/1985 | Cone . |
| 4,720,148 | 1/1988 | Anthony et al. . |
| 4,790,601 | 12/1988 | Burleigh et al. .......... 297/484 |
| 4,858,997 | 8/1989 | Shubin ................... 297/484 X |
| 4,874,203 | 10/1989 | Henley ................... 297/464 X |
| 5,002,338 | 3/1991 | Gisser . |
| 5,120,103 | 6/1992 | Kave . |
| 5,158,337 | 10/1992 | Leggett ................. 297/250.1 |

FOREIGN PATENT DOCUMENTS

| | | | |
|---|---|---|---|
| 2001415 | 11/1971 | Germany ................ 297/464 |
| 282034 | 7/1952 | Switzerland ............ 297/363 |
| 2171 | 7/1867 | United Kingdom ..... 297/363 |
| 1301595 | 12/1972 | United Kingdom ..... 297/464 |

OTHER PUBLICATIONS

6-A Pediatrics—Kiddie Litter®, Jems, Feb. 1988.
Advertising flyer entitled "Why the Carrie® LifeSeat®?", 1990.
Article entitled "Trends" from Motor Trend Magazine, Dec. 1991.

*Primary Examiner*—Peter R. Brown
*Attorney, Agent, or Firm*—Killworth, Gottman, Hagan & Schaeff

[57] ABSTRACT

A multiple position child restraint device for use with vehicles, stretchers, cots, beds, and other transport apparatuses, and which can be folded into planar condition for storage and shipment. The restraint device includes substantially planar back support, seat support, and leg support members hingedly attached in serial relationship with one another generally along a longitudinal axis. The hinged connection between the back support and seat members is preferably provided by a pair of oppositely disposed hinges having a plurality of locking slots which align with one another at predetermined angular relationships, and wherein a locking bar fits within the aligned slots to selectively lock the back support and seat members in one of a plurality of predetermined angular orientations. A multiple strap restraint device including a pair of shoulder straps and a releasable buckle secures the child on the seat and back support members, and an arrangement is provided for convenient adjustment of the shoulder straps along the longitudinal length of the back support member to accommodate children of different sizes without disconnecting the straps from the device. Folding lateral support panels are also provided along the opposite longitudinal edges of the seat and back support members.

31 Claims, 3 Drawing Sheets

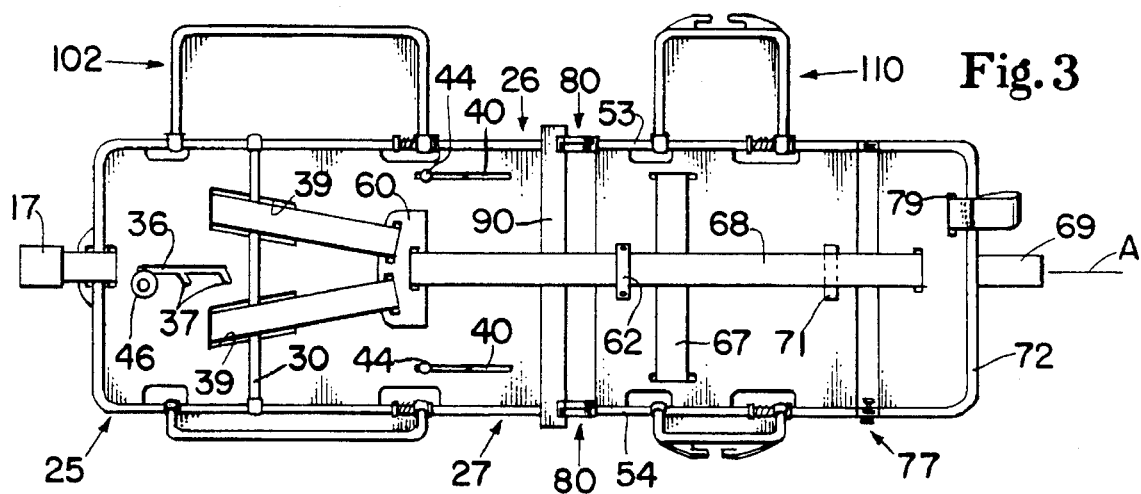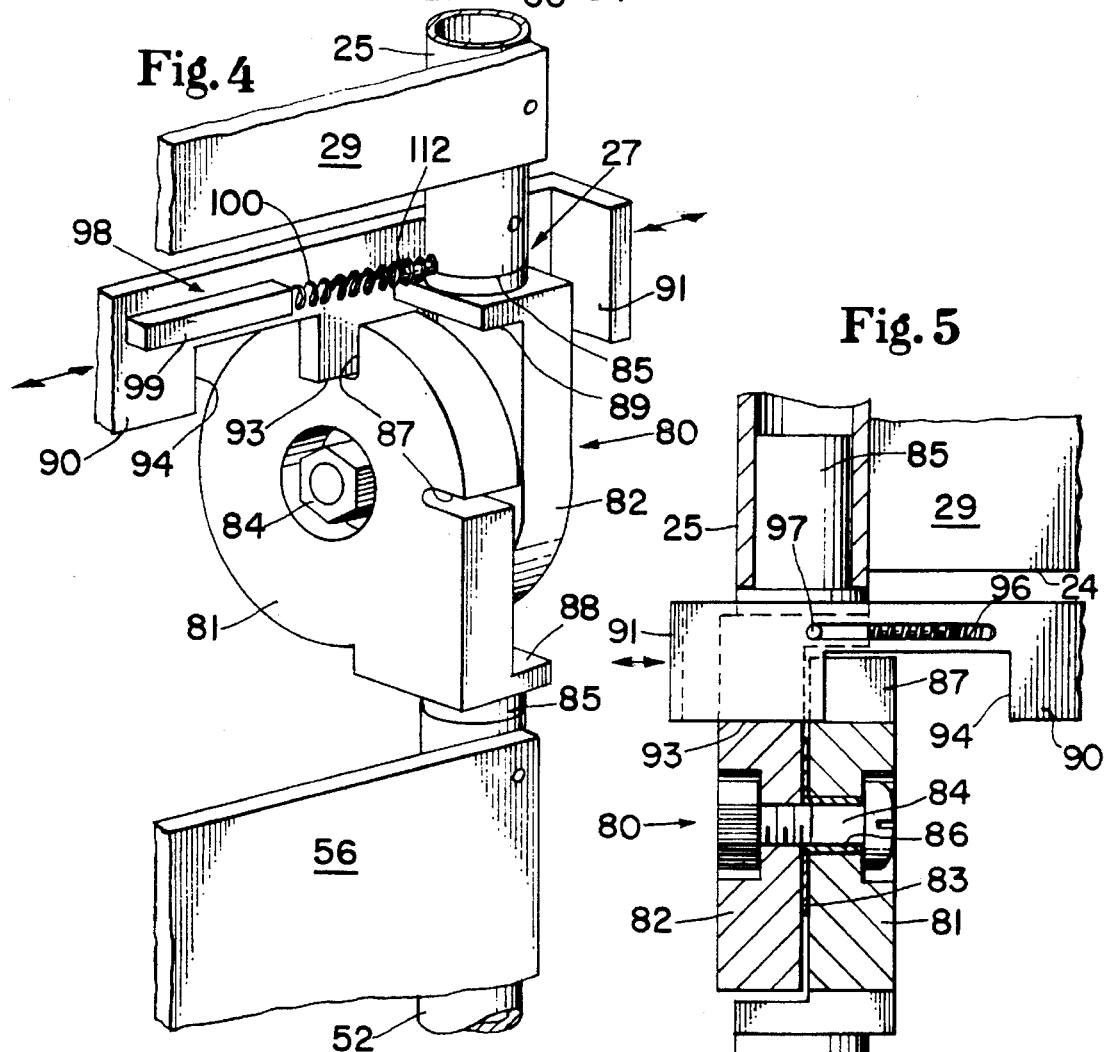

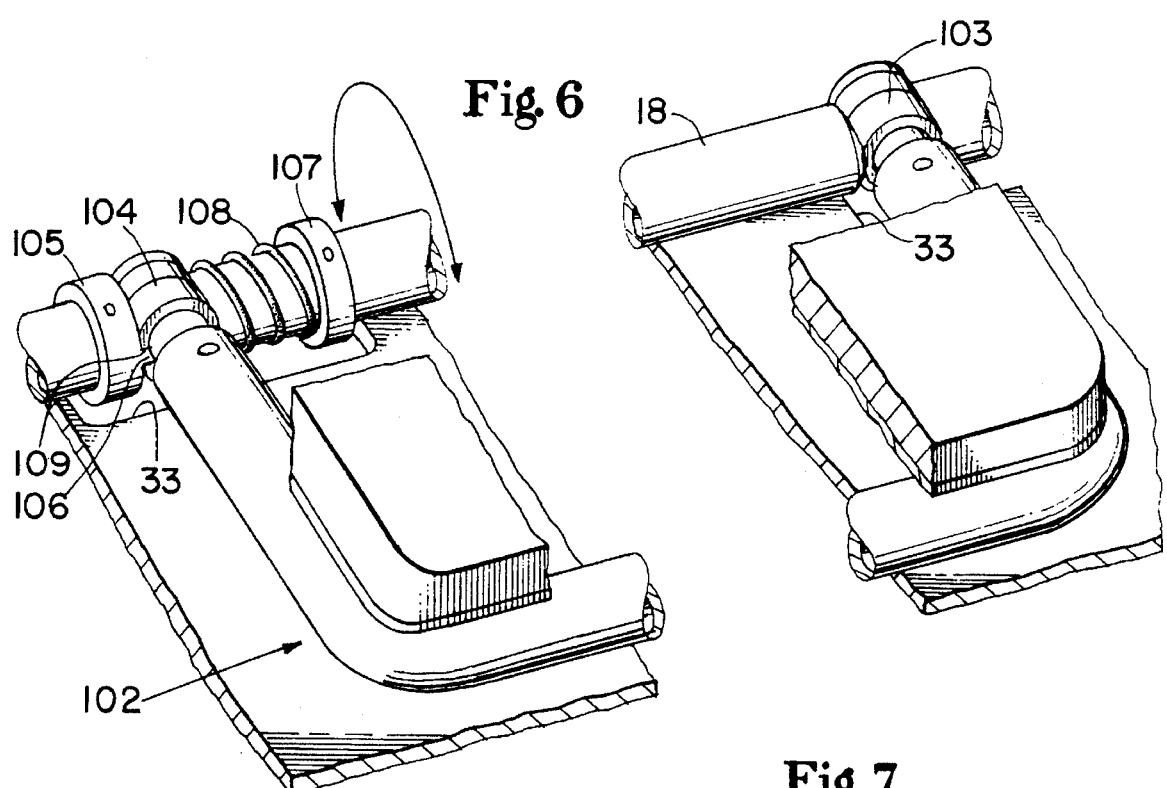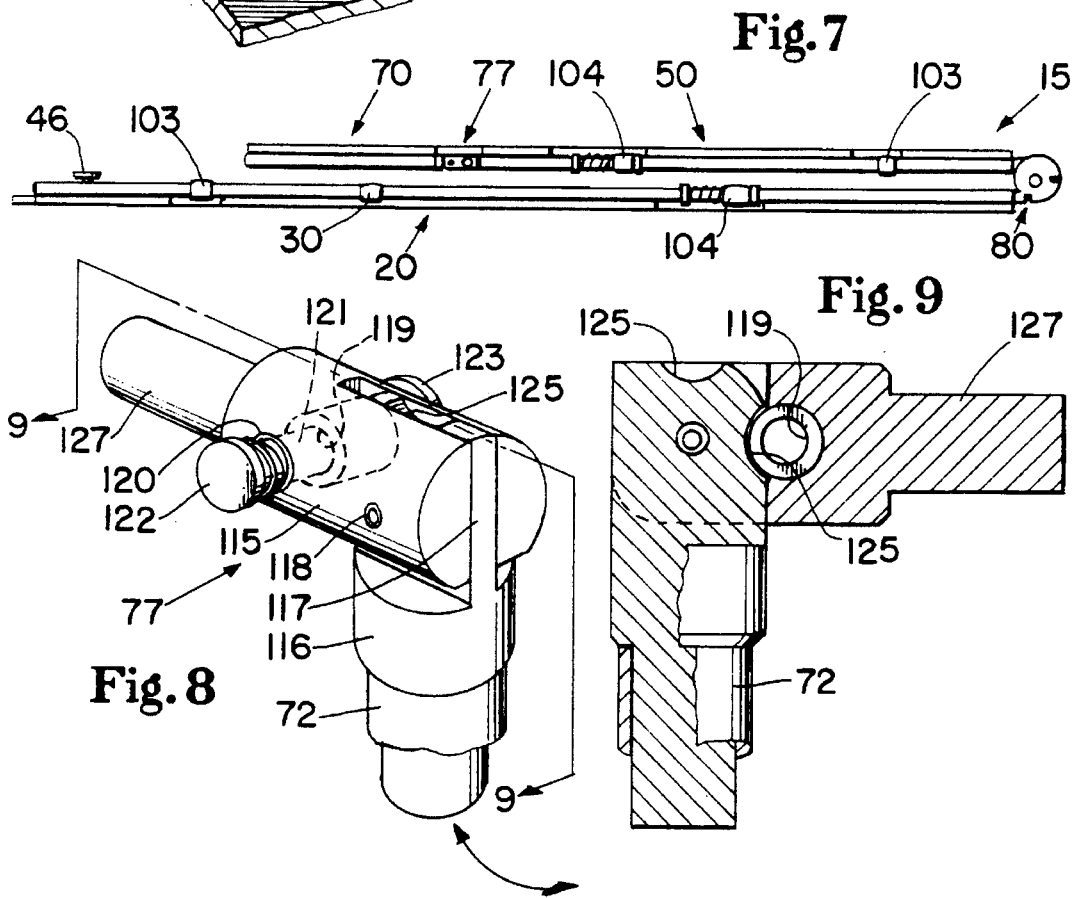

MULTI-POSITION PEDIATRIC IMMOBILIZER AND TRANSPORT DEVICE

This is a continuation of application Ser. No. 07/879,852, filed May 6, 1992 now abandoned.

TECHNICAL FIELD

This invention relates to devices for immobilizing and/or securely restraining a child for transportation or immobilization in motor vehicles, aircraft, and other modes of transportation, or on stretchers or other transport apparatuses, and, more particularly, to a pediatric restraining seat for use in emergency vehicles and with related emergency equipment which features multiple immobilizing or restraining positions as well as improved adaptability to children of varying sizes and foldability for compact storage and transportation.

BACKGROUND ART

While continued improvements in technology and procedures has precipitated many changes in the construction, organization, and use of the wide range of equipment and procedures commonly associated with emergency vehicles such as ambulances, air transport devices and the like, reliability and storage requirements are always critical in selection of equipment available. While crash stable pediatric restraint and immobilizing devices are generally desirable and required in many emergency rescue and transportation situations, as well as other every day situations such as commercial air transportation and simple vehicular transportation and commuting, the various devices available in the prior art generally suffer from excessive size, bulk, degree of complication, and/or cost, which inhibits their widespread use.

For example, U.S. Pat. No. 4,181,356 (which issued to H. Fleischer) discloses a folding baby carrier which comprises a plurality of parts which can be folded into a flat arrangement. However, this carrier does not provide any restraint system, nor does it provide structure for reliably holding the child in a plurality of positions for safe, comfortable and/or convenient transportation. Similarly, while U.S. Pat. No. 4,058,342 (which issued to J. Ettridge) shows a foldable child's car seat, the device is relatively complex and bulky, and lacks means for easily adapting the seat to a wide range of child sizes.

A wide variety of child safety carriers and seats have also been available for use in conjunction with motor vehicle transportation. For example, U.S. Pat. No. 4,274,674 (which issued to B. Deloustal) illustrates an example of a reclinable safety seat which can be anchored within a motor vehicle. The Deloustal safety seat provides several predetermined reclining positions, and two trough shaped half shells of semi-rigid synthetic material are hingedly connected to provide the main portions of the seat for supporting a child. A plurality of slots are provided in the half shells through which various straps for securing and holding the child in the seat can be threaded. As with a number of the other child safety seats available in the marketplace, however, this device is relatively bulky, requires a relatively large amount of space for storage and non-use transport, and requires a relatively cumbersome procedure of removing and rethreading support straps for children of different sizes.

Another child restraint device is shown in U.S. Pat. No. 5,002,338 (which issued to M. Gisser) comprising a base and a hinged flap which can be locked in planar configuration to support the child, and folded over for carrying and storing the restraint. This device further includes a plurality of wing panels which extend from sides of the hexagonal base member which can serve as walls surrounding the child in use, as well as a five point restrain harness system. This system, however, is designed for lap-top use or attached facing a chair back as shown in FIG. 7 of the patent. Consequently, this device is practically limited to use for small infants, and its base and flap must remain in planar configuration in use, thereby limiting its applicability.

Devices have also been specifically designed for use in emergency vehicles and the like, such as the child safety support sold under the name KIDDIE LITTER (a trademark of Dixie), which includes a rigid base, a back support piece and a leg support piece which can be assembled in several angular orientations by a plurality of upstanding side support members. The KIDDIE LITTER seat is designed to reduce to a flat position for storage, and its various pieces can be snapped together in a plurality of orientations for supporting a child in various positions. Foam mattresses can be adhesively applied to the upper surfaces of the device for additional comfort. However, this assembly does not provide for optimum strength and rigidity in use, and requires a plurality of pieces which must be snapped together or assembled for each use. Additionally, while the KIDDIE LITTER includes a plurality of openings for adjusting its restraint harness members, such adjustment is relatively cumbersome and requires inconvenient disconnection and/ or removal of the harness members for threading through individual slots.

Other devices, such as the Carrie LifeSeat (as available from Tumbleforms, Inc., Clifton, N.J.) provide immobilization and/or restraint for pediatric rescue and transportation applications, however, have similar problems of complexity, bulkiness, assembly and/or storage requirements.

Consequently, while the need for providing safe, reliable, and convenient child safety restraint and immobilization devices has clearly existed for quite some time, the products available heretofore have generally been too complicated, too big, too cumbersome, and/or difficult or impossible to quickly adapt to a variety of recurring applications and varying child sizes. Others, such as the built-in child seats which have recently become available in certain automobiles, are dedicated use type devices which cannot be transported or adapted to a variety of vehicles and applications.

DISCLOSURE OF THE INVENTION

It is an object of the present invention to obviate the above-described problems and shortcomings of the child safety restraint devices heretofore available in the industry.

It is also an object of this invention to provide an improved device for restraining and/or immobilizing a child during transport by emergency vehicle, aircraft, or the like.

It is yet another object of the present invention to provide a portable, foldable and multi-position pediatric immobilizer and transport device which features a relatively simple structure which is easy to adapt to a variety of emergency equipment, vehicle applications and user sizes.

It is another object of the present invention to provide a pediatric immobilizer and transport device which provides optimum support of the child at one of a plurality of supine or sitting positions in conjunction with a variety of vehicles, stretchers, cots, beds, seats, or other transport apparatuses without requiring structural reconfiguration of the device.

It is yet an additional object of the present invention to provide a foldable pediatric transport device which is capable of folding flat for transportation or storage, and reducing into a compact relatively flat position of reduced longitudinal length to further facilitate convenient storage and transport.

In accordance with one aspect of the present invention, there is provided a multiple position child restraint device for use with vehicles and transportation devices, stretchers, cots, beds, and the like, and which can be folded into planar condition for storage and shipment. The restraint device includes a substantially planar back support, seat support, and leg support members hingedly attached in serial relationship with one another generally along a longitudinal axis. The hinged connection between the back support and seat members preferably comprises a pair of oppositely disposed hinges having a plurality of locking slots which align with one another at predetermined angular relationships, and wherein a locking bar fits within the aligned slots to selectively lock the back support and seat members in one of a plurality of predetermined angular orientations. A multiple strap restraint device including a pair of shoulder straps and a releasable buckle secures the child on the seat and back support members, and an arrangement is provided for convenient adjustment of the shoulder straps along at least a portion of the longitudinal length of the back support member to accommodate children of different sizes without disconnecting the straps from the device.

In a preferred embodiment, the arrangement for adjusting the shoulder straps along the back support member includes a reciprocable shoulder strap adjustment plate overlying a portion of the back support member and situated for selective longitudinal movement to adjust the position of the shoulder straps.

The restraint device also preferably includes a plurality of folding side support panels located along opposite longitudinal edges of the back support member and the seat member. These support panels are further preferably mounted for rotation among a plurality of predetermined locking positions for providing additional flexibility for use, attachment, and storage of the restraint device. The leg support member is also preferably hingedly connected for relatively easy adjustment among a plurality of angular orientations relative to the seat member.

BRIEF DESCRIPTION OF THE DRAWINGS

While the specification concludes with claims particularly pointing out and distinctly claiming the present invention, it is believed the same will be better understood from the following description taken in conjunction with the accompanying drawings in which:

FIG. 3 is a bottom plan view of the device of FIG. 2, further illustrating several of the various positions of the side support panels;

FIG. 4 is a partial, enlarged perspective view of a preferred hinge/locking arrangement between the seat and back support members of a pediatric immobilizer and transport device of the present invention, viewed generally from the front of the device;

FIG. 5 is a partial, enlarged cross-sectional view of the hinge/locking arrangement of FIG. 4, viewed from the rear or backside of the device;

FIG. 6 is a partial, enlarged perspective view of a preferred lateral support panel mounting and locking arrangement of the present invention;

FIG. 7 is a side elevational view of a pediatric immobilizer and transport device of the present invention, shown in its fully folded position;

FIG. 8 is an enlarged perspective view of a multi-position lockable hinge which can be used to attach the leg support member to the seat member of the present system; and FIG. 9 is a partially broken out cross-sectional view of the hinge of FIG. 8, showing the details of a preferred multi-position lock and release mechanism.

DETAILED DESCRIPTION OF THE INVENTION

Figure 1:
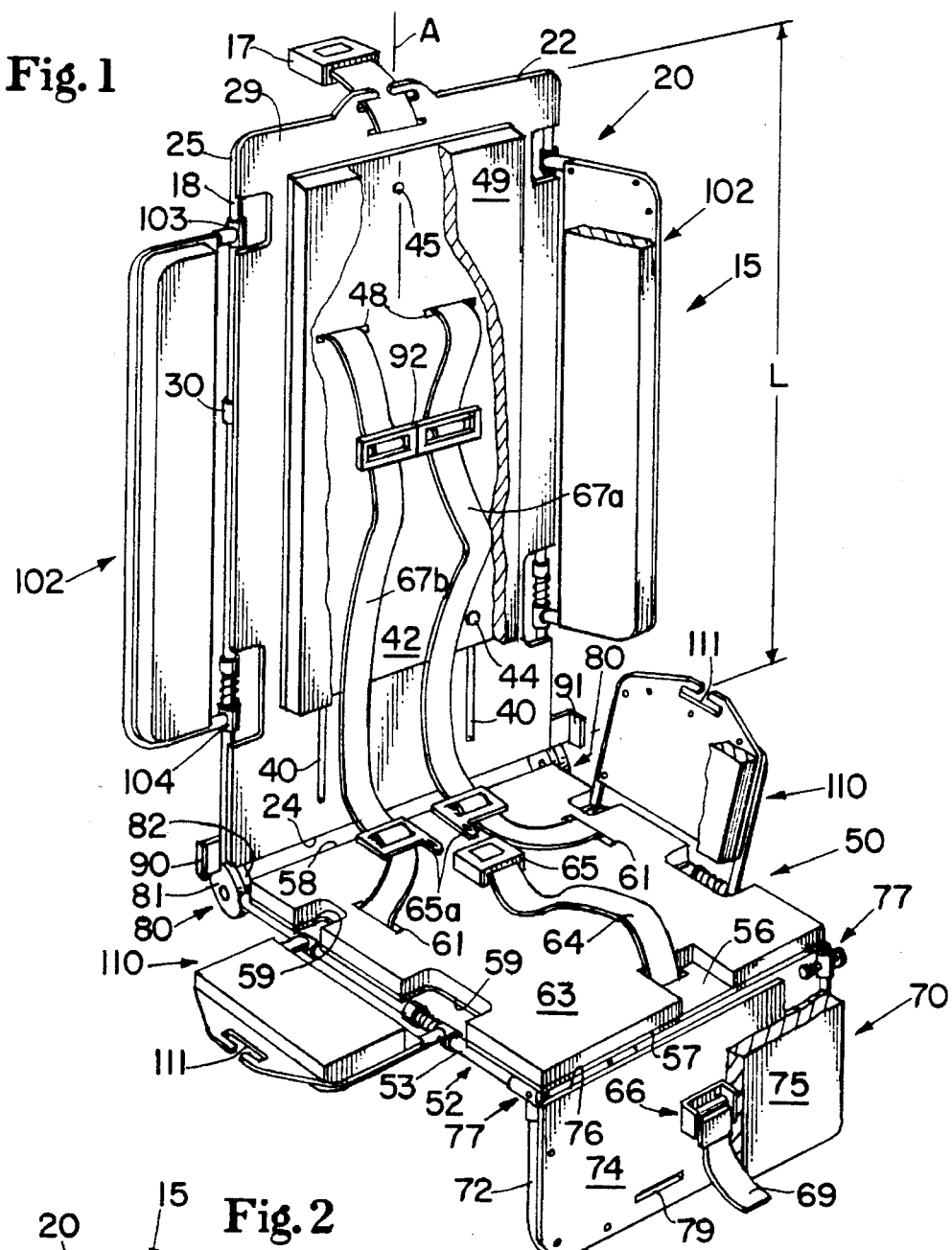
FIG. 1 is a partially broken out, perspective view of a pediatric immobilizer/transport device of the present invention, shown in its sitting or chair position.

Referring now to the drawings in detail, wherein like numerals indicate the same elements throughout the views, FIG. 1 illustrates a partial perspective view of a multiple position pediatric child restraint and transport device 15 of the present invention. Further details of a preferred embodiment of the subject restraint device are illustrated in FIGS. 2–9. Looking first to FIGS. 1–3, the child restraint device 15 is illustrated as preferably comprising a sub-frame made of generally tubular support stock (e.g., 18) provided with relatively rigid cover members, as will be explained. Restraint device 15 broadly comprises a back support member (e.g., 20), a seat support member (e.g., 50), and a leg support member (e.g., 70) longitudinally and serially attached in a hinged manner for manipulation among a plurality of in-use and storage positions.

Back support member ,20 is preferably provided as a substantially planar member having an upper edge 22 and a lower edge 24. Back support tubular frame 25 is shown as comprising a single, unitary length of tubular stock (18) configured to define a relatively rectangular back support 20, although several members could alternately be combined as frame 25. Tubular frame 25 includes opposite ends 26 and 27, respectively (as best seen in FIGS. 3 and 4), and has a back support base plate or panel 29 attached about the forwardly oriented peripheral portions thereof. Back support base plate 29 can preferably take the form of a sheet of metallic, synthetic, composite, wood or other substantially rigid material.

Plate 29 could alternatively be provided in a form of a flexible or resilient fabric, although it is preferred that it be relatively rigid for optimum performance characteristics, durability, and cleanability. While it is also contemplated that each of the main support members (e.g., 20, 50 and 70) could each be provided of an integrally formed or even unitary (e.g., one piece molded plastic or the like) form, panel 29 is illustrated as being connected to tubular frame 25, such as by pop rivets, adhesive, welding, or other convenient manner. Along opposite longitudinal edges (e.g., 31 and 32) of base plate 29, a plurality of openings 33 are preferably provided to accommodate attachment and rotative adjustment of lateral support panels (e.g., 102) as will be described below. A means (34) for facilitating attachment of transport device 15 to other structures can be provided in the form of a slot, as illustrated. A quick attachment strap 17 (shown in FIGS. 1 and 3) may also be anchored to device 15 through slot 34, such as a female buckle member, and may optionally be removable as desired.

As best illustrated in the bottom plan view of FIG. 3, an adjustment gate 36 is provided along the upper portions of base panel 29, substantially along longitudinal axis A. Particularly, adjustment gate 36 is a preferred means for providing a plurality of predetermined locking locations (e.g., 37) along the longitudinal length L of back support member 20 to facilitate quick adjustment of the positioning of a pair of shoulder straps (e.g., 67a and 67b) in order to accommodate children of varying sizes. The number of locking locations 37, of course, will be determined by the number adjustment positions desired.

A pair of spaced, longitudinally elongated shoulder strap feed-through openings 39 are provided in base panel 29 for receiving the opposite distal ends of harness strap 67. These openings will also preferably be inwardly angled toward one another along axis A, whereby longitudinal adjustment of the shoulder straps also automatically laterally adjusts the effective spacing or width between the, straps, as will be further described below.

It is preferred that a unitary harness strap 67 be utilized, wherein the center of strap 67 is positioned below seat support member 50, and the opposite distal ends of strap 67 are fed through a pair of spaced harness openings 61 to provide a pair of shoulder straps 67a and 67b, and then threaded through respective shoulder strap feed-through opening 39 for attachment to a seat belt connector bar 60 or similar device for common connection and control. At least portions of the various straps utilized with the subject restraint device and immobilizer may preferably be non-porous in nature to provide enhanced hygienic characteristics and to facilitate cleanup of the device between uses. To provide that non-porous feature, fabric straps may need to be coated or covered, as appropriate.

It is contemplated that seat belt connector bar 60 could be provided in a form similar to that shown in U.S. Patent Des. 285,383 (which issued to J. Anthony). In this way, shoulder straps 67a and 67b can be commonly tightened and loosened via a single cinch strap 68 connected at its proximal end (68a) to connector bar 60, having its distal end (69) threaded through a belt retractor device (e.g., 66) for convenient and dependable tightening and securement thereof. Belt retractor 66 can be provided in various forms available in the industry, such as shown and described in U.S. Pat. No. 4,720,148 (which issued to J. Anthony et at.).

Referring again to FIGS. 1 and 2, means are preferably provided on back support member 20 for selectively adjusting shoulder straps 67a and 67b along the longitudinal length L to accommodate children of different sizes without disconnecting or removing the strap restraints from the transport device 15. In a preferred arrangement, the means for providing adjustability to the shoulder straps includes a substantially planar adjustment plate (e.g., shoulder strap support 42) coveting a portion of the front surface of panel 29 and provided with a pair of spaced guide pins 44 slidably received within corresponding spaced longitudinal guide slots 40 formed within back support 20 and generally parallel with longitudinal axis A. Adjacent its upper portions, adjustment plate 42 is connected through adjustment gate 36 via a pin 46 and locking connector or knob 45 combination.

Particularly, pin 46 (which might be a carriage type bolt) is anchored at its proximal end to adjustment plate of strap support 42, extends through adjustment gate 36, and is threadably connected to locking knob 45. When tightened onto pin 46, knob 45 binds adjustment plate 42 against back support member 20 to prevent further movement therebetween. As illustrated, the distal portions of locking locations 37 are preferably slightly downwardly angled to facilitate adjustment procedures and more securely maintain pin 46 in a locked position.

A pair of spaced relatively horizontal shoulder strap slots 48 are provided through which shoulder straps 67a and 67b are threaded. By loosening knob 45, adjustment plate 42 can be reciprocated longitudinally relative to base panel 29, thereby adjusting the relative longitudinal position of the upper portions of shoulder straps 67a and 67b. As moved longitudinally, adjustment plate 42 correspondingly adjusts the longitudinal position of the shoulder straps 67a and 67b, as the slots 48 are raised or lowered along axis A. It is preferred that the width of slots 48 will be substantially greater than the width of straps 67a and 67b, respectively, so that longitudinal movement of the straps along the angled guide slots 39 in base plate 29 automatically and simultaneously laterally adjusts the shoulder straps toward or away from one another. As will be appreciated, this lateral movement provides automatic and corresponding adjustment of the effective width of the spacing between the uppermost portions of the shoulder straps to optimally accommodate children of varying sizes.

As best seen in FIG. 3, shoulder straps 67a and 67b preferably pass over a brace 30, which extends between opposite sides of frame 25. Brace 30 provides additional support for back member 20, and further serves to guide the shoulder straps during adjustment procedures. The location of brace 30 approximately midway along the longitudinal adjustment height of slots 48 also provides further backup support of the shoulder straps adjacent base plate 29.

Once adjusted to a desired longitudinal location, knob 45 is tightened along gate 36 to prevent further movement of adjustment plate 42. It should be understood that this knob/pin combination is illustrated only as a preferred example of a quick release locking arrangement for adjustment plate 42. Other lock/release mechanisms could equally be substituted in appropriate situations.

A harness restraint 92 is also illustrated as an optional means for maintaining the respective shoulder straps 67a and 67b in close proximity to one another is use. It is preferred that harness restraint 92 be slidable along the shoulder straps for easy adjustment, and can include release means to enable detachment of at least one side of the harness from the straps. Maintaining the straps in relatively close relation ensures that the straps remain in appropriate restraining position on a child in use.

FIG. 1 further illustrates (in broken out section) a preferred arrangement wherein a pad 49 is provided over a substantial portion of the front surfaces of back support member 20 to augment comfort and safety features of the device. It is contemplated that pad 49 might have a size corresponding generally to adjustment plate 42 and connected to plate 42 for adjustable reciprocation therewith. Pad 49 would, of course, preferably be provided with a contour and openings sufficient to accommodate the various conformation, harness straps and movable parts of restraint device 15.

Seat support member 50 is illustrated as a substantially rectangular and planar assembly having a tubular frame 52 comprising a pair of spaced and substantially parallel frame members 53 and 54, respectively. A relatively rigid seat plate or panel 56 is preferably attached to the upper periphery of tubular frame 52, wherein panel 56 further defines front and rear seat edges 57 and 58, respectively. A plurality of openings 59 along the opposite longitudinal edges of seat member 50 accommodate the rotatable lateral support panels (110), as will be discussed below. As indicated in broken out section, a pad member (e.g., 63) may also preferably cover a substantial portion of seat member 50 for added comfort and safety.

A harness center or crotch member 64 is preferably connected to seat panel 56 (e.g., at anchor 71), and includes a multi-clasp buckle 65 for releasably receiving seat belt type locking tongues (e.g., 65a) of the respective shoulder straps 67a and 67b. In this way, a child can be quickly and conveniently placed on restraint device 15 with shoulder straps 67a and 67b disconnected from harness member 64, and easily thereafter strapped within the device by appropriate connection of the buckle and locking tongues. Once appropriately buckled within the restraint device 15, shoulder strap 67a and 67b can be appropriately snugged up by tightening of the distal end 69 through belt retractor 66 and harness restraint 92 longitudinally adjusted as necessary. As seen best in FIG. 3, one or more cinch strap guides (e.g., 62) can be provided along the rear face of seat panel 56 to maintain cinch strap 68 in optimum alignment.

Leg support member 70 similarly comprises a tubular frame 72 and a leg support panel or plate 74 joined to the frame. Tubular frame 72 preferably again comprises a substantially unitary, single piece support tube, which, with panel edge 76 defines a substantially rectangular and planar leg support member 70. As mentioned, a belt retractor or similar harness tightening device 66 is preferably supported on leg support member 70 for convenient access to those supervising the restraint and transportation of the child held within the subject restraint device 15. A pad member 75 may similarly be provided for additional comfort and protection of the user. While not shown, additional flexible and/or extensible coverings or support members could further be provided to span any gaps between adjacent transverse edges between the back and seat members (e.g., between edges 24 and 58) and between the seat and leg support members (e.g., between edges 57 and 76). Such members might take the form of removable stretch support material such as neoprene, elasticized canvas or the like, or other resilient and supportive material.

As best illustrated in FIGS. 4 and 5, back support member 20 and seat support member 50 are preferably hingedly connected adjacent their lower and rear edges by a pair of oppositely disposed hinges 80, each comprising a pair of relatively rotatable hinge members 81 and 82 connected for relative rotation by a connector (e.g., 84). A wear pad 83 may preferably minimize contact wear between members 81 and 82, and a sleeve 86 can be located (e.g., by press fit or the like) to receive and align connector 84. Tube connectors 85 provide rigid connection of frame members (e.g., distal end 27 of frame member 25) to one of the adjacent hinge members (e.g., 82) for rotation. As mentioned, a means for selectively locking back support 20 and seat support member 50 against forward and rearward movement in one of a plurality of predetermined angular orientations preferably provides a corresponding plurality of predetermined restraint and storage positions for restraint device 15.

Figure 2:
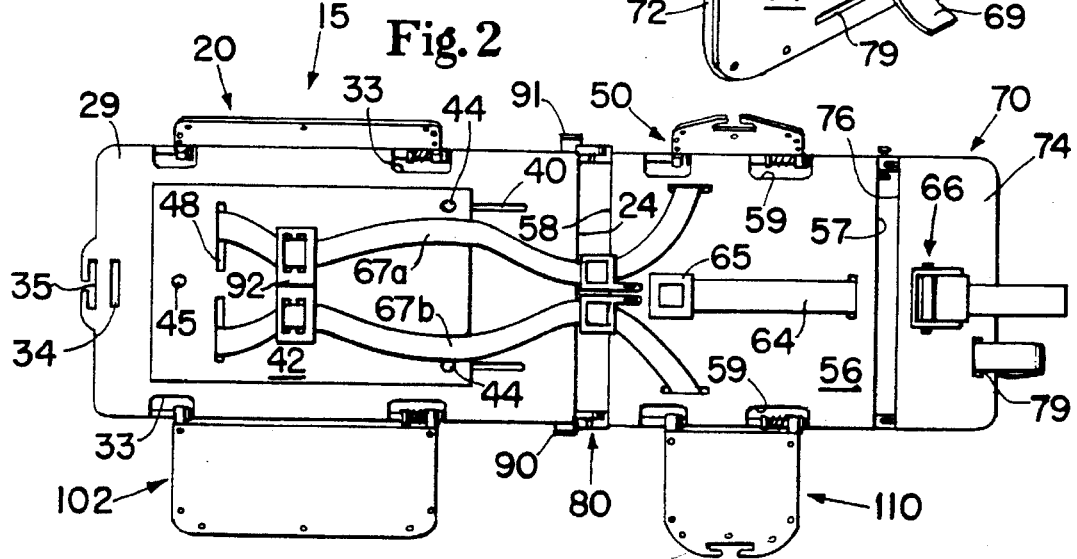
FIG. 2 is a top plan view of the device of FIG. 1, shown in a planar position and with its pads removed.

For example, FIG. 7 illustrates the fully folded position of restraint device 15, wherein leg support member 70 and seat support member 50 are oriented in a relatively co-planar orientation with one another, and are folded in an overlapping planar arrangement with back support member 20 with the inner surfaces (e.g., the rear surface of member 20 and the rearface of member 50) of these members in substantially face-to-face relationship. As indicated in FIG. 7, this fully compacted folded position is accomplished by counter-clockwise rotation of the seat and leg support members about hinges 80. FIG. 1, on the other hand, illustrates a chair or seated position, wherein back support member 20 is oriented at about a 90° angle to seat support member 50. FIGS. 2 and 3 further illustrate the supine or planar position of restraint device 15 wherein back support member 20 is rotated into a substantially planar orientation with, seat support member 50 and leg support member 70. This position can be utilized for prone restraint or immobilization of a child, or storage of the device in its compact and planar condition.

In order to selectively lock the back and seat support members in the various predetermined angular relationships, a plurality of locking slots 87 are preferably provided for intermittent interlocking/release interaction with a slidable locking bar 90. Locking bar 90 further comprises a release lever 91 for convenient manipulation by a user, a lower locking edge 93, and a release recess 94 provided adjacent hinge 80. Locking bar 90 is preferably slidably attached adjacent at least one of the hinges 80 for limited transverse movement, such as by the slot 96 and attachment pin 97 arrangement seen best in FIG. 5. Additionally, bar 90 is normally biased to its locked position by a biasing arrangement (e.g., 98), which might comprise a spring retainer 99 and compression spring 100 telescoped over an alignment nub (e.g. 112 in FIG. 4) on frame 25. Transverse movement of locking bar 90 moves release recess 94 outwardly until locking edge 93 no longer resides within the locking slot 87 of hinge member 81. At this time, the respective hinge members 81 and 82 can be rotated relative to one another to modify the angular orientation of the back and seat support members.

Any number of locking slots 87 can be provided about the periphery of locking member 81 to provide desired angular locking positions. Once rotated to a desired angular orientation, release pressure on locking bar 90 is removed, whereupon locking edge 93 will again slide into the aligned locking slots 87 of both hinge members 81 and 82 to lock the seat and back members against rotation. Outwardly extending rotation stops (e.g. stops 88 and 89) can also be provided to positively stop and support hinge 80 in one or more desired angular orientation. For example, stops 88 and 89 are illustrated as providing interfacing flanges which serve to strengthen hinge 80 in its upright or seated position (i.e. when the back support is oriented at approximately 90 degrees to the seat support). It should be understood that the bar and slot arrangement is provided only as a preferred illustration, and that other selectively lockable hinge arrangements can equally be substituted to provide dependable means for selectively locking the back and seat support members in the desired angular orientations.

As will be understood, and as best illustrated in FIGS. 1, 4, 5 and 7, in order to enable the present restraint device to reliably provide a plurality of supine, seated, and compact storage positions, and use in conjunction with a variety of vehicles, stretchers, cots, beds, seats, or other transport apparatuses without requiring structural reconfiguration of the device, the hinges (e.g., 80) and locking device (e.g., 90) are preferably mounted between the back and seat support members in a non-protruding or substantially flush condition (i.e., substantially flush with the respective substantially planar structure of these members ) with the restraint device members. This arrangement enables all of the contemplated functions without interference and inconvenience.

Turning now to FIG. 6, a preferred arrangement for rotatably and selectively lockingly mounting a plurality of lateral support panels (e.g. panels 102 and 110) along the longitudinal edges of back support member 20 and/or seat support member 50 is illustrated. Particularly, an exemplary support panel 102 is illustrated as including a rotatable sleeve connection 103 for rotatably supporting the panel on a tubular support (e.g., 18). A sleeve 104 is similarly provided at the opposite end of support panel 102, however, this sleeve further preferably comprises means for selectively locking panel 102 in one of a plurality of orientations with respect to the adjacent support member. A preferred locking means illustrated as part of sleeve 104 comprises one or more lock recess 109 spaced about the lower edge of sleeve 104 and facing locking retainer 105. Particularly, locking retainer 105 preferably comprises a ring-like structure attached about the periphery of tubular support 18 (such as by set screw, adhesive, welding or the like) to limit the longitudinal movement of support panel 102 (or 110, etc.) therealong.

Retainer 105 further comprises one or more inwardly extending lock nubs or protuberances 106 spaced about its inner edge to correspond with and lockingly engage recesses 109 of sleeve 104. A spaced retainer 107 is connected to tubular support 18, and a spring 108 is compressively placed between retainer 107 and sleeve 104 to normally bias sleeve 104 toward retainer 105. As will be appreciated, selective rotation of a support panel can only be accomplished upon compression of spring 108 and movement of sleeve 104 out of locking engagement with retainer 105. Again, any number of angular locking positions can be provided by this selective locking arrangement, and other appropriate radial locking members or ratchet locking devices can be equally substituted to enable this controlled rotatability of support panels made in accordance herewith.

As seen in the various drawing figures, it is contemplated that a pair of oppositely disposed lateral support panels (e.g. 102 and 110) will preferably be provided along the longitudinal edges of each of the back and seat support members, although any number of such panels could be provided. Additionally, similar rotatable side supports or wings could also be provided along leg support member 70. As seen best in FIGS. 3, 6 and 7, it is also preferred that where lateral support panels are provided (e.g. panels 102 and 110), that they also be rotatable to a folded position substantially flush with the back side of restraint device 15 to facilitate storage and transportation procedures, and so that such support panels will not interfere with use of device 15 when they are not required or desired to be in an upright position. The support panels 110 adjacent seat member 50 may each also comprise a belt retainer (e.g. retainers 111, as seen in FIG. 1) to receive restraint devices such as seat belts or straps commonly found in vehicles and on transport apparatuses.

It is contemplated that leg support member 70 will similarly be hingedly connected adjacent front edge 57 of seat support member 50 by a pair of oppositely disposed hinges 77. In order to accommodate a variety of use positions and child sizes, it is further preferred that hinges 77 be of a multi-position locking type. While these hinges may preferably take a form similar to hinges 80 with a locking bar similar to bar 90 described above, any of a number of multiply positionable locking hinges having pushbutton release mechanisms or the like could also be utilized. A preferred multi-position locking hinge for leg support members 70 is illustrated in FIGS. 8 and 9. Particularly, hinge 77 is shown as featuring a pair of bayonet-like hinge members 115 and 116, wherein the blade portion of hinge member 116 is rotatably connected within the corresponding slot of member 115 by pin 118. A spring loaded locking finger 121 is fitted in a bore 119 and designed to selectively prevent rotation of the joint by way of an intermittent interlocking relationship with one of the spaced scallops 125 formed about the outer periphery of blade 117 of hinge member 116. When locking finger 121 is in its biased locking position within bore 19, it resides within an aligned scallop and interferes with rotation of hinge members 15 and 116; while, when pressed inwardly against spring 120, the parts are free to rotate for adjustment. Finger 121 can be depressed inwardly by inward pressure on button 122, or by outward manipulation of pull knob 123. Hinge 77 is attached to respective tubular seat and leg support frame members via male connectors 127, similar to connectors 85 described above.

Tie down means such as slot 79 (and, possibly, an access loop as illustrated in FIGS. 2 and 3) can optionally be provided adjacent the seat and/or leg support members to accommodate attachment devices for securing device 15 to other transport devices such as cots, beds, stretchers or the like. As seen best in FIGS. 1 and 2, one or more retainer openings 35 can optionally be provided along upper edge 22 of back support 20 to receive and retain standard restraining equipment such as a shoulder harness of a motor vehicle to help secure device 15 in conjunction with other transport apparatuses and vehicles. For example, a shoulder harness might be threaded through retainer 35 to provide additional anchoring and retention, as well as conveniently keeping the shoulder harness from interfering with the optimum use and function of restraint device 15.

Having shown and described the preferred embodiments of the present invention, further adaptions of the multiple position pediatric immobilizer and transport device shown and described herein can be accomplished by appropriate modifications by one of ordinary skill in the art without departing from the scope of the present invention. Many of such potential modifications have been mentioned, and others will be apparent to those skilled in the art. For example, as mentioned, each of the back, seat and leg support members of the present invention might be provided with their frame and covering panels formed as single piece, unitary parts which can be quickly assembled into the present restraint device. Such parts might be made of lightweight, strong materials, and their one piece construction would facilitate manufacture, repair and replacement procedures. Accordingly, the scope of the present invention should be considered in terms of the following claims, and is understood not to be limited to the details of structure and operation shown and described in the specification and drawings.

We claim:

1. A multiple position child restraint device which can be folded into substantially planar condition for storage and shipment, said restraint device comprising:

a substantially planar back support member having a longitudinal length and upper and lower edges along that length and a rear surface;

a substantially planar seat support member having front and rear edges and a rear face, said seat support member attached to said back support member adjacent said rear and lower edges, respectively, by a hinge assembly;

a leg support member pivotally attached adjacent said front edge of said seat support member;

means associated with said back support and seat support members for selectively locking said back support and seat support members against forward and rearward movement in one of a plurality of predetermined angular orientations, said leg support member and said seat support member being adapted to be oriented in a substantially coplanar relationship and be folded in an overlapping planar arrangement with said back support member with the rear face of said seat support member and the rear surface of said back support member in substantially face-to-face relationship without a need for structural reconfiguration; and a multiple strap restraint means for securing a child on said seat and back support members, said restraint means attached to said restraint device and comprising a pair of shoulder straps and a releasable buckle arrangement for selective connection with a crotch member strap on said restraint device.

2. The restraint device of claim 1, wherein said hinge assembly comprises one or more hinges and said means for selectively locking said back support and said seat members in a desired angular orientation comprises a locking bar which selectively interlocks with said one or more hinges connecting said back and seat members.

3. The restraint device of claim 3, wherein said hinge assembly comprises a pair of oppositely disposed hinges connecting said seat and back members, and wherein said locking bar slidably and selectively interlocks with aligned locking slots in at least one of said hinges to prevent further rotation thereof.

4. The restraint device of claim 1, further comprising means on said back support member for adjusting said shoulder straps along the longitudinal length to accommodate children of different sizes without disconnecting said strap restraint means, and wherein said adjusting means comprises a longitudinally reciprocable shoulder strap support overlying a portion of said back support member.

5. The restraint device of claim 4, wherein said shoulder strap support comprises a substantially planar adjustment plate having a pair of spaced harness slots through which said shoulder straps are individually supported, whereby longitudinal movement of said adjustment plate along said back support member correspondingly adjusts the position of said shoulder straps.

6. The restraint device of claim 4, further comprising means for securing said shoulder strap support in one of a plurality of predetermined longitudinal positions along said back support member.

7. The restraint device of claim 6, wherein said securing means comprises a guide slot and guide pin arrangement for maintaining said shoulder strap support in alignment during reciprocation along said back support member, and means for selectively locking said shoulder strap support in one of a plurality of longitudinal positions along said back support member.

8. The restraint device of claim 1, further comprising a pair of lateral support panels located along opposite longitudinal edges of said back support member, said panels being hingedly connected and rotatable relative to said back support member and lockable in a plurality of angular positions relative thereto.

9. The restraint device of claim 8, further comprising a pair of lateral support panels located along opposite longitudinal edges of said seat member, said panels being hingedly rotatable among a plurality of lockable angular positions relative to said seat member.

10. The restraint device of claim 9, further comprising a rear surface on said back support member and a rear face on said seat support member, wherein said lateral support panels are hingedly rotatable into a storage position which is substantially planar with said back support member and said seat support member, respectively.

11. The restraint device of claim 1, further comprising means for selectively fixing and maintaining said leg support member in one of a plurality of angular orientations relative to said seat member.

12. The restraint device of claim 1, further comprising means in said back support member for automatically adjusting the lateral spacing between said shoulder straps when said shoulder straps are longitudinally adjusted.

13. A multiple position child restraint device which can be folded into a relatively planar compact condition for storage and shipment, said restraint device comprising:

a tubular frame defining a substantially planar and rectangular back support member having a longitudinal length, and front and rear surfaces, and upper and lower edges along that length, a substantially planar and rectangular seat support member having front and rear edges, and front and rear faces, and a leg support member pivotally attached adjacent said front edge of said seat support member;

at least one hinge for hingedly attaching said seat support member to said back support member adjacent said lower and rear edges, respectively;

means associated with said at least one hinge for selectively locking said back support and seat members in one of a plurality of predetermined angular orientations, said means comprising a locking bar which selectively interlocks with at least one hinge connecting said back and seat members, and means for enabling said back support member and said seat support member to be rotated relative to one another into an overlapping, substantially planar storage condition, wherein the rear surface of the back support member and corresponding rear face of said seat member are folded into substantially face-to-face relationship;

a multiple strap restraint means for securing a child on said seat and back support members, said restraint means attached to said restraint device and comprising a pair of shoulder straps and a releasable buckle arrangement for selective connection with a crotch member strap on said restraint device; and a pair of lateral support panels located along opposite longitudinal edges of at least one of said back support and seat support members, said panels hingedly connected thereto and rotatable and lockable in a plurality of positions.

14. The restraint device of claim 13, further comprising means on said back support member for adjusting said shoulder straps along the longitudinal length to accommodate children of different sizes without disconnecting said strap restraint means from said device.

15. The restraint device of claim 12, further comprising means on said back support member for adjusting said shoulder straps along the longitudinal length to accommodate children of different sizes without disconnecting said strap restraint means, and wherein said adjusting means comprises a longitudinally reciprocable shoulder strap support overlying a portion of said back support member.

16. The restraint device of claim 15, further comprising means for securing said shoulder strap support in one of a plurality of predetermined longitudinal positions along said back support member.

17. The restraint device of claim 16, wherein said securing means comprises a guide slot and guide pin arrangement for maintaining said shoulder strap support in alignment during reciprocation along said back support member, and means for selectively locking said shoulder strap support in one of a plurality of longitudinal positions along said back support member.

18. The restraint device of claim 12, further including a shoulder strap support, and wherein said shoulder strap support comprises a substantially planar adjustment plate having a pair of spaced harness slots through which said shoulder straps are individually supported, whereby longitudinal movement of said adjustment plate along said back member correspondingly adjusts the position of said shoulder straps.

19. The restraint device of claim 18, further comprising a pair of longitudinally angled guide slots which automatically adjust the lateral distance between said shoulder straps when said adjustment plate is longitudinally moved.

20. The restraint device of claim 12, further comprising a pair of lateral support panels located along opposite longitudinal edges of both said seat and back support members.

21. The restraint device of claim 20, wherein said lateral support panels are hingedly rotatable into a storage position which is substantially planar with said back support member and said seat support member, respectively.

22. The restraint device of claim 13, further comprising means for selectively fixing and maintaining said leg support member in one of a plurality of angular orientations relative to said seat member.

23. A multiple position child restraint device for use with seats, stretchers, and other transport apparatuses, and which can be folded into a plurality of compacted conditions for storage and shipment, said restraint device comprising:

a substantially planar back support member having a longitudinal length, and front and rear surfaces, and upper and lower edges along that length;

a substantially planar seat support member having front and rear edges, and front and rear faces;

a leg support member pivotally attached adjacent said front edge of said seat support member;

at least one hinge for hingedly attaching said seat support member to said back support member adjacent said lower and rear edges, respectively;

means associated with said at least one hinge for selectively locking said back support and seat members in one of a plurality of predetermined angular orientations, and means for enabling said back support member and said seat support member to be rotated relative to one another into an overlapping, substantially planar storage condition, wherein the rear surface of the back support member and the corresponding rear face of said respective back support members are folded into substantially face-to-face relationship;

a multiple strap restraint means for securing a child on said seat and back support members, said restraint means attached to said restraint device and comprising a pair of laterally spaced shoulder straps and a releasable buckle arrangement for selective connection with a crotch member strap on said restraint device;

means on said back support member for adjusting said shoulder straps along the longitudinal length to accommodate children of different sizes without disconnecting said strap restraint;

a pair of lateral support panels located along opposite longitudinal edges of said back support member, said panels hingedly connected thereto and rotatable relative to said back support member and lockable into a plurality of angular positions relative thereto; and a pair of lateral support panels located along opposite longitudinal edges of said seat member, said seat panels being hingedly rotatable among a plurality of lockable angular positions relative to said seat member.

24. The restraint device of claim 23, wherein said adjusting means comprises a longitudinally reciprocable shoulder strap support overlying a portion of said back support member.

25. The restraint device of claim 24, wherein said shoulder strap support comprises a substantially planar adjustment plate having a pair of spaced harness slots through which said shoulder straps are individually supported, whereby longitudinal movement of said adjustment plate along said back member correspondingly adjusts the position of said shoulder straps.

26. The restraint device of claim 25, wherein said back support member comprises a pair of longitudinally angled guide slots through which said shoulder straps extend, whereby the lateral space between said shoulder straps is automatically adjusted when said adjustment plate is moved longitudinally.

27. The restraint device of claim 22, wherein said lateral support panels are hingedly rotatable into a storage position which is substantially planar with said back support member and said seat support member, respectively.

28. A multiple position child restraint device which can be folded into substantially planar condition for storage and shipment, said restraint device comprising:

a substantially planar back support member having a longitudinal length and upper and lower edges along that length;

a substantially planar seat support member having front and rear edges, said seat support member attached to said back support member adjacent said rear and lower edges, respectively, by a hinge assembly;

means associated with said back and seat support members for selectively locking said back support and seat support members in one of a plurality of predetermined angular orientations, including, particularly a planar condition for use in conjunction with beds, cots, stretchers, and the like without a need for structural reconfiguration;

a multiple strap restraint means for securing a child on said seat and back support members, said restraint means attached to said restraint device and comprising a pair of shoulder straps and a releasable buckle arrangement for selective connection with a crotch member strap on said restraint device; and further comprising a rear surface on said back support member and a rear face on said seat support member, wherein said hinge assembly comprises a pair of selectively lockable rotating hinges, and wherein said hinges comprise means for enabling said seat and back support members to be rotated into overlapping, substantially planar storage condition, with said respective rear face of said seat support member and rear surface of said back support member in substantially face-to-face relationship.

29. A multiple position child restraint device which can be folded into a plurality of supine and seated positions, as well as into a longitudinally compacted substantially planar position for storage and shipment, said restraint device comprising:

a substantially planar back support member having front and rear surfaces, a longitudinal length, and upper and lower edges spaced along said longitudinal length;

a substantially planar seat support member having front and rear edges and front and rear faces;

a rotatable hinge for hingedly attaching said rear edge of said seat support member adjacent said lower edge of said back support member to enable adjustment of angular orientation therebetween;

a leg support member attached adjacent said front edge of said seat support member;

means for selectively locking said back and seat support members into one of a plurality of predetermined angular orientations, said locking means interacting with said hinge to enable selective adjustment of said angular orientation;

an adjustable multiple strap releasable restraint means for securing a child on said seat and back support members in use; and said hinge being located between said back and seat support members and substantially flush with said respective surfaces and faces thereof, whereby said back support member and said seat support member can be rotated relative to one another into an overlapping, substantially planar compacted storage condition with their respective rear surface and rear face elements in face-to-face relationship, without interference of protruding structure and without a need to structurally reconfigure the restraint device.

30. The restraint device of claim 29, wherein said hinge enables relative rotation of said back and seat support members up to approximately 270° between a seated position where said seat and back support members are generally perpendicular to one another and said overlapping, substantially planar storage condition where said seat and back support members are generally parallel to one another.

31. A multiple position child restraint device which can be folded into a substantially planar condition for storage and shipment, said restraint device comprising:

a substantially planar back support member having a longitudinal length and upper and lower edges along that length and a rear surface;

a substantially planar seat support member having front and rear edges and a rear face, said seat support member attached to said back support member adjacent said rear and lower edges, respectively, by a hinge assembly;

a locking device associated with said back support and seat support members which locks said back support and seat support members against forward and rearward movement in one of a plurality of predetermined angular orientations, said seat support member being adapted to be folded in an overlapping planar arrangement with said back support member with the rear face of said seat support member and the rear surface of said back support member in substantially face-to-face relationship without a need for structural reconfiguration; and a multiple strap restraint attached to said restraint device and comprising a pair of shoulder straps and a releasable buckle arrangement for selective connection with a crotch member strap on said restraint device.

* * * * *

UNITED STATES PATENT AND TRADEMARK OFFICE
CERTIFICATE OF CORRECTION

PATENT NO. : 5,496,092
DATED : Mar. 5, 1996
INVENTOR(S) : Williams et al.

It is certified that error appears in the above-indentified patent and that said Letters Patent is hereby corrected as shown below:

Col. 11, Line 20, "claim 3" should be --claim 2--.
Col. 12, Line 52, "claim 12" should be --claim 13--.
Col. 13, Line 3, "claim 12" should be --claim 13--.
Col. 13, Line 14, "claim 12" should be --claim 13--.
Col. 14, Line 20, "claim 22" should be --claim 23--.

Signed and Sealed this

Twenty-eighth Day of May, 1996

Attest:

BRUCE LEHMAN

Attesting Officer     Commissioner of Patents and Trademarks